(12) United States Patent
Jaha

(10) Patent No.: US 11,324,776 B2
(45) Date of Patent: May 10, 2022

(54) MAILLARD REACTION PRODUCTS AS INHIBITORS OF AGGREGATIBACTER ACTINOMYCETEMCOMITANS

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Raniah Abdulmohsen Afif Jaha, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

(*) Notice: Subject to any disclaimer, the term of this patent is extended or adjusted under 35 U.S.C. 154(b) by 128 days.

(21) Appl. No.: 16/819,889

(22) Filed: Mar. 16, 2020

(65) Prior Publication Data
US 2021/0283154 A1    Sep. 16, 2021

(51) Int. Cl.
*A61K 35/02* (2015.01)
*A61P 31/04* (2006.01)
*A61P 1/02* (2006.01)
*A61K 31/7012* (2006.01)

(52) U.S. Cl.
CPC .......... *A61K 35/02* (2013.01); *A61K 31/7012* (2013.01); *A61P 1/02* (2018.01); *A61P 31/04* (2018.01)

(58) Field of Classification Search
None
See application file for complete search history.

(56) References Cited

U.S. PATENT DOCUMENTS 9,993,414 B2    6/2018    Hao et al.

FOREIGN PATENT DOCUMENTS

KR    10-2016-0094485    8/2016

OTHER PUBLICATIONS

Shao et al., "Autoinducer 2 Is Required for Biofilm Growth of Aggregatibacter (*Actinobacillus*) actinomycetemcomitans" Infection and Immunity vol. 75 No. 9 pp. 4211-4218 (Year: 2007).*
Kundinger et al., "Effects of Maillard Reaction Products on hilA Expression in *Salmonella* Typhimurium" Journal of Food Science vol. 73 No. 1 pp. M32-M35 (Year: 2008).*
Cuzzoni et al., "Influence of Water Activity and Reaction Temperature of Ribose-Lysine and Glucose-Lysine Maillard Systems on Mutagenicity, Absorbance and Content of Furfurals" Food and Chemical Toxicity vol. 26 No. 10 pp. 815-822 (Year: 1988).*

(Continued)

*Primary Examiner* — Eric Olson
(74) *Attorney, Agent, or Firm* — Oblon, McClelland, Maier & Neustadt, L.L.P.

(57) ABSTRACT

Maillard reaction products produced by heating carbohydrates with one or more amino acids (e.g., lysine), at basic pH and for a selected reaction time at a particular concentration in solution, can exhibit inhibitory activity against *Aggregatibacter actinomycetemcomitans*.

17 Claims, 2 Drawing Sheets

(56) References Cited

OTHER PUBLICATIONS

Bhattacharjee, et al. ; Microwave sterilization of growth medium alleviates inhibition of Aggregatibacter actinomycetemcomitans by Maillard reaction products ; Journal of Microbiological Methods, vol. 78, Issue 2 ; pp. 227-230 ; Aug. 2009 ; Abstract Only ; 2 Pages.
Karipay ; Inhibition of Growth of the Periodontal Bacteria Aggregatibacter Actinomycetemcomitans by Mallard Reactions Products ; 2017 ; 9 Pages.
Bhattacharjee, et al. ; Does microwave sterilization of growth media involve any non-thermal effect? ; Journal of Microbiological Methods 96 ; pp. 70-72 ; Nov. 15, 2013 ; Abstract Only ; 3 Pages.

\* cited by examiner

MAILLARD REACTION PRODUCTS AS INHIBITORS OF AGGREGATIBACTER ACTINOMYCETEMCOMITANS

BACKGROUND OF THE INVENTION

Field of the Invention

The present disclosure relates to formulations for the inhibition of *Aggregatibacter actinomycetemcomitans* growth, particularly using Maillard reaction products, including the product of a Maillard reaction between lysine and glucose in solution, e.g., using a 1.5:1 to 1:1.5 molar ratio, for example in a reflux pump above 90° C. in a solvent preferably comprising water.

Description of the Related Art

The Maillard reaction, named after the French chemist, Louis-Camille Maillard, is a chemical reaction between one or more amino acids and one or more reducing sugars, which reaction gives browned food its distinctive flavor. Many foods, including seared meats, such as grilled steaks, sausages, and hamburgers, fried dumplings, cookies, biscuits, breads, roasted marshmallows, etc., undergo this reaction.

The Maillard reaction is a non-enzymatic browning reaction which typically proceeds rapidly from around 140 to 165° C., and most cooking recipes (particularly oven recipes) employ temperatures high enough to ensure that a Maillard reaction occurs. At higher temperatures, beyond the Maillard reaction threshold, caramelization (the browning of sugars, a distinct process), and beyond the caramelization threshold, pyrolysis or breakdown leading to burning and $CO_2$ generation, begins to predominate.

In the Maillard reaction, the reactive carbonyl group of the sugar, often an aldehyde, reacts with the nucleophilic amino group of the amino acid, and forms a complex mixture of typically poorly characterized molecules that are responsible for a variety of scents and flavors. The Maillard reaction is accelerated in an alkaline environment, i.e., basic pHs—below 7, such as with lye applied to darken pretzels), as the normally protonated amino groups of amino acids, i.e., $RNH_3^+$, become deprotonated, i.e., $RNH_2$. As a consequence of the deprotonation, the amine groups on the amino acids have an increased nucleophilicity.

In cooking processes, Maillard reactions can produce hundreds of different flavor compounds depending on the chemical constituents in the food, the temperature, the cooking time, and the presence of air (or oxygen). These flavor compounds, in turn, often break down to form yet more flavor compounds. Flavor scientists have used the Maillard reaction over the years to make artificial flavors.

As a general concept, laboratory Maillard reaction products (MRPs) can be obtained from mixing any carbohydrate or mixture thereof with any amino acid or mixture thereof upon heating. Each amino acid will react with each carbohydrate in a different way, which will not result with the same exact end products. MRPs reactions can result in thousands of components with thousands of different effects when using different mixtures, different amounts, different processing, and the like.

There are many types of carbohydrates and a variety of (natural) amino acids, offering access to a broad array of totally different products and effects. Even the same carbohydrates with the same amino acids give different reactions and effects if they are heated or processed under different conditions.

While Maillard reaction products (MRPs) have had a variety of applications in the food and flavoring industries, only a limited amount of research has been conducted into their potential antibacterial applications.

U.S. Pat. No. 9,993,414 to Hao et al. (Hao) discloses oral care compositions and methods of inhibiting microbial biofilm formation and/or degrading a microbial biofilm. Hao's oral care compositions comprise an Amadori compound having a glucose moiety and an amino acid moiety, obtainable from a reaction of a ketose sugar with an amino acid. Hao's Amadori compound can inhibit oral microbial biofilm formation and/or degrade an oral microbial biofilm in the oral cavity of a mammalian subject. Hao's composition may comprise the reaction product of reacting D or L-glucose with alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. While described as optional, Hao's composition is not described to contain any more than 10 wt. % of the Amadori product. Hao does not indicate a particularly useful amino acid, nor the inhibition of *Aggregatibacter actinomycetemcomitans* with Hao's product.

KR 10-2016-0094485 A by Lee et al. (Lee) discloses a composition containing a Maillard reaction product as an active ingredient for alleviating bowel function or anti-inflammation. Lee reports its Maillard reaction product to improve intestinal microflora by increasing the proliferation of useful enterobacteria, *Lactobacillus* and *Bifidobacterium* strains, and to inhibit the proliferation of harmful *Clostridium* strains and powerfully suppress the expression of inflammatory cytokines in inflammatory reaction. Lee's composition can be used for health functional foods and feed additives to alleviate bowel function and for drugs and healthy functional foods to prevent or treat a bowel disease or inflammatory diseases caused by an imbalance of enterobacteria. Lee's reagents may include unlimited numbers of amino acids, such as pyrrolysine, selenocysteine, peptides/proteins, food by-products or other by-products including them, or unlimited sugars include, but are not limited to, glucose, fructose, galactose, sucrose, maltose, lactose, xylose, ribose, deoxyribose, ribitol, etc., polysaccharides, food by-products, or other by-products including them. Lee is silent about using a Maillard reaction product to inhibit *Aggregatibacter actinomycetemcomitans*.

*J. Microbiol. Meth.* 2009, 78(2), 227-230 by Bhattacharjee et al. (Bhattacharjee I) discloses Maillard reaction products formed by autoclaving a mixture of lysine and glucose and their use to inhibit growth of *Aggregatibacter* (*Actinobacillus*) *actinomycetemcomitans*, the causative agent of localized aggressive periodontitis and endocarditis. Bhattacharjee I reports that a difference between autoclaved and microwaved media is that the autoclaved media are darker brown in color, which is known to be due to the Maillard reaction products. Bhattacharjee I does not describe solution-based Maillard reactions, nor the particular selection of reaction conditions used to obtain a material suitable to inhibit the growth of *A. actinomycetemcomitans*.

The master's thesis entitled, "Inhibition of Growth of the Periodontal Bacteria *Aggregatibacter actinomycetemcomitans* by Maillard Reaction Products," submitted at the Long Island University Department Chemistry and Biochemistry by Deepa Karipay (Karipay) discloses inhibiting bacterial growth by Maillard reaction products, i.e., Amadori products. Karipay reports that sugar-derived protein adducts and cross-links known as advanced glycation end-products (AGEs) inhibit the growth of both the smooth and rough strains of *A. actinomycetemcomitans* both in plates and in broth, but that adding FeCl$_3$ restores growth of the bacteria, even in the presence of the Maillard reaction products. Karipay does not describe particular solution-based Maillard reactions, nor the particular selection of reaction conditions used to obtain a material suitable to inhibit the growth of *Aggregatibacter actinomycetemcomitans*.

*J. Microbiol. Meth.* 2014, 76, 70-72 by Bhattacharjee et al. (Bhattacharjee II) discloses fast reactions mediated by microwaves for the rapid formation of Maillard reaction products. Bhattacharjee II reports that microwave sterilization of growth medium results from concentration effect and not any non-thermal effect, describing microwave synthesis as an improved method for microwave sterilization of growth media. Bhattacharjee II does not describe particular solution-based Maillard reactions, nor the particular selection of reaction conditions used to obtain a material suitable to inhibit the growth of *Aggregatibacter actinomycetemcomitans*.

In light of the above, a need remains for compositions for inhibiting the proliferation of *Aggregatibacter actinomycetemcomitans*, particularly with materials made by biologically benign materials, such as lysine, glucose, and water, heated, preferably in a reflux pump and adjusted pH of 7.5, and methods of making such inhibitors.

SUMMARY OF THE INVENTION

Aspects of the invention provide method for inhibiting growth of *Aggregatibacter actinomycetemcomitans* comprising administering an isolated Maillard reaction product obtained by a process comprising reacting glucose with an amino acid, preferably lysine, preferably in a molar ratio in a range of from 0.5 to 0.95:1 in solution. Such methods and products may be modified by any permutation of the features described herein, particularly the following.

The inhibiting the growth may comprise treating an oral infection or an infection of the heart, such as endocarditis, involving *Aggregatibacter actinomycetemcomitans*. The oral infection may be gingivitis or periodontitis.

The reacting may comprise heating the solution at a temperature in the range of from 90 to 100° C., optionally in the presence of boiling chips.

The reacting may be conducted as a basic pH, wherein the pH is preferably in a range of 7.01 to 8.

The reacting may be conducted such that no more than 5 wt. % of the solvent is lost in the reaction. The reacting may be conducted using a reflux pump.

The solution may comprise, relative to all carbohydrates present in the solution, at least 90 wt. % of the glucose. The basic amino acid is preferably lysine. The solution may comprise, relative to all amino acids present in the solution, at least 90 wt. % lysine. The reacting may comprise heating a mixture consisting essentially of glucose and lysine at a temperature in a range of from 90 to 100° C., preferably in a reflux pump with an adjusted pH of about 7.5 in the presence of boiling chips.

The solution may comprise at least 90 wt. % of water, preferably distilled water, relative to total solvent weight.

The glucose and the basic amino acid may each be present in a concentration range of from 0.75 to 1.5 M in the solution.

The reacting may be conducted for a reaction time in the range of from 20 to 90 minutes.

The inhibiting of the growth of *Aggregatibacter actinomycetemcomitans* may comprise allowing no more than 5% of the *Aggregatibacter actinomycetemcomitans* growth relative to an untreated culture space. The inhibiting may be in an oral cavity or the heart, such as on the valves of the heart.

Aspects of the invention provide isolated Maillard reaction products which may be obtained by a process in a reflux pump comprising reacting glucose with an amino acid such as lysine in a molar ratio in a range of from 0.5 to 0.95:1 in water, preferably at a pH of about 7.5 with the presence of boiling chips.

Aspects of the invention provide methods for inhibiting growth of *Aggregatibacter actinomycetemcomitans* comprising contacting the *Aggregatibacter actinomycetemcomitans* with any permutation of the Maillard reaction product or of the inventive Maillard processes described herein.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
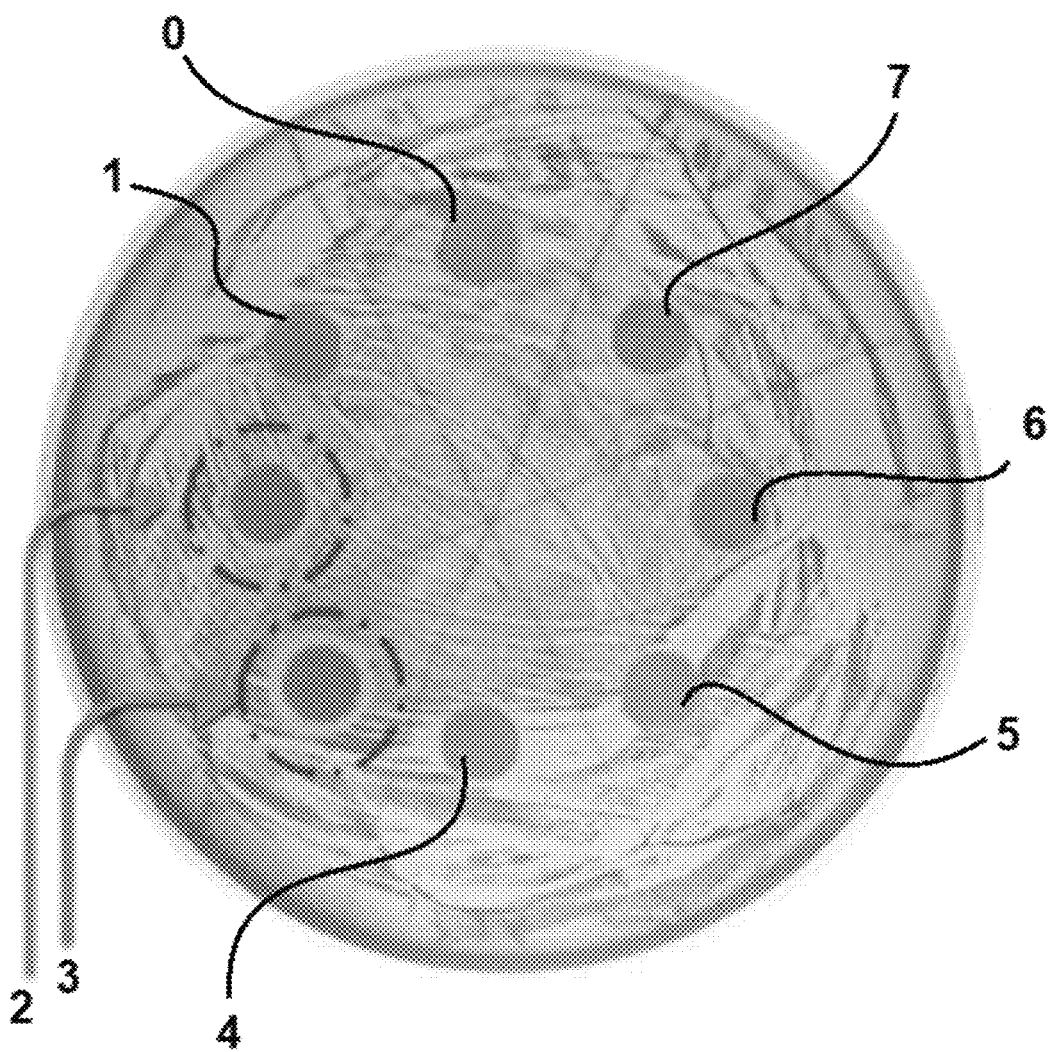
FIG. 1 shows a Petri dish containing *Aggregatibacter actinomycetemcomitans* growth medium (AAGM) with the *Aggregatibacter actinomycetemcomitans* results relative to the Maillard reaction product (MRP) spots corresponding to reactions of different reaction times.

Aspects of the invention provide method for inhibiting (up to preventing or substantially preventing) the growth of *Aggregatibacter actinomycetemcomitans* comprising administering an isolated Maillard reaction product, typically containing several Maillard reaction products, preferably obtained by a process comprising reacting glucose with an amino acid lysine such as lysine in a molar ratio in a range of from 0.5 to 0.95:1 in solution, particularly distilled water in aqueous solution using a reflux pump. The glucose may be in a molar ratio, relative to the basic amino acid, for example, of at least 0.5, 0.55, 0.575, 0.6, 0.625, 0.65, 0.675, 0.7, 0.7125, 0.725, 0.733, 0.7375, 0.75, 0.7625, 0.767, 0.775, 0.7875, 0.8, 0.8125, 0.825, 0.833, 0.8375, or 0.85 and or up to 0.95, 0.925, 0.9, 0.8875, 0.875, 0.867, 0.8625, 0.85, 0.8375, 0.825, 0.8125, 0.8, 0.7875, 0.775, 0.767, 0.7625, 0.75, 0.7375, 0.733, 0.725, 0.7125, or 0.7. The basic amino acid may comprise at least 75, 80, 85, 90, 91, 92, 92.5, 93, 94, 95, 96, 97, 97.5, 98, 99, 99.1, 99.5, or 99.9 wt. %, relative to the total weight of the amino acids in solution, of (for example, arginine, and/or histidine), preferably lysine, though β-, γ-, and/or δ-amino acids may be included. L-enantiomers of the amino acids may be preferred for price considerations, but D-enantiomers may also be useful, as may racemic mixtures.

The inhibiting of the growth of *Aggregatibacter actinomycetemcomitans* may comprise treating Endocarditis or an oral infection involving *Aggregatibacter actinomycetemcomitans*, such as, for example, gingivitis and/or periodontitis. The *Aggregatibacter actinomycetemcomitans* (wild type) may be, e.g., of the a strain, b strain, or c strain serotype, such as ATCC 29523, ATCC 33384, b strain Y4, and/or b subtype Jp2. MRPs within the scope of the invention may inhibit the growth of further Gram-negative bacteria and/or coccobacillary bacteria, such as *Haemophilus*

*aphrophilus, Haemophilus paraphrophilus,* and/or *Haemophilus segnis,* and/or *Escherichia coli, Salmonella, Shigella,* other Enterobacteriaceae, *Pseudomonas, Moraxella, Helicobacter, Stenotrophomonas, Bdellovibrio,* acetic acid bacteria, *Legionella,* cyanobacteria, spirochaetes, green sulfur, green non-sulfur bacteria, *Neisseria gonorrhoeae, Neisseria meningitidis, Moraxella catarrhalis, Haemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis, Salmonella typhi, Acinetobacter baumannii, Vibrio cholerae, Ralstonia solanacearum,* and/or *Xylella fastidiosa.*

Inventive compositions may comprise the MRPs, typically in a sterilized and/or distilled water and/or saline solution, and drugs that have gram negative spectrum including, e.g., cephalosporins, monobactams (aztreonam), aminogylosides, quinolones, macrolides, chloramphenicol, folate antagonists, and/or carbapenems.

The reacting may comprise heating the solution at a temperature in the range of from 90 to 100° C., e.g., at least 90, 91, 92, 93, 94, 95, 96, or 97° C. and/or up to 103, 102, 101, 100, 99.5, 99, 98.5, 98, or 97.5° C., optionally in the presence of boiling chips (i.e., boiling stones). The boiling chips may be made of alumina, silicon carbide, calcium carbonate, calcium sulfate, and/or porcelain. Typically the reaction to form the Maillard reaction products will be conducted at or near the solvent's reflux temperature, e.g., reflux ±0.1, 0.15, 0.2, 0.25, 0.33, 0.35, 0.4, 0.45, 0.5, 0.67, 0.75, 1, 1.5, 2, or 2.5° C. The heating is preferably from conductive means, preferably in the reflux pump only, and may use heating from an oil jacket, water bath, steam bath, oil bath, metal bath, or heating mantel, rather than convective, or electromagnetic, e.g., microwaves, IR, or the like.

The reacting may be conducted as a basic pH, wherein the pH may be in a range of 7.01 to 8, preferably about 7.5. Suitable pHs for the reaction may be, for example, at least 7.0001, 7.01, 7.05, 7.1, 7.15, 7.2, 7.25, 7.3, 7.33, 7.35, 7.4, 7.45, or 7.5, and/or up to 8, 7.95, 7.9, 7.85, 7.8, 7.75, 7.7, 7.65, 7.625, 7.6, 7.55, or 7.5. The adjustment of the pH may be carried out by adding a weak base and/or a weak acid, as the concentration of amino acid may necessitate, such as acetic acid (or an acetate salt), formic acid (or a formate salt), lactic acid (or a lactate salt), citric acid (or a citrate salt) ammonium chloride, ammonium bromide, ammonium hydroxide, ammonia, phosphoric acid (or a phosphate salt), NaHSO$_4$, bicarbonate, or the like, including combinations of these. The salts may include, e.g., ammonium, tetraalkyl ammonium, pyridinium, sodium, potassium, magnesium, and/or lithium.

The reacting may be conducted such that no more than 5, 4, 3, 2.5, 2, 1, 0.5, 0.1, 0.01, 0.001, 0.0001, or 0.00001 wt. %, relative to total solvent weight, of the solvent, e.g., is lost in the reaction. The reacting may be conducted using a reflux pump and/or devices to maintain the amount of solvent present in the reaction, such as in a closed system. The reacting may be conducted under an atmosphere of air, or under an inert environment, such as under Ar, He, N$_2$, or a combination of these. The reacting may be conducted at ambient pressure or e.g., at least 0.9, 0.95, 1, 1.05, 1.1, 1.15, 1.2, 1.25, 1.5, 2, 2.5, 3, 4, or 5 bar-a and/or up to 10, 7.5, 7, 6.5, 6, 5.5, 5, 4.5, 4, 3, 2, 1.5, or 1.25 bar-a. The pressure is typically held static during the reacting, as is typically the volume/mass of solvent. For example, either or both of the pressure and/or the solvent mass is typically held at 90, 91, 92, 92.5, 93, 94, 95, 96, 97, 97.5, 98, 99, 99.1, 99.5, or 99.9% of (or the same as) the original value.

The solution may comprise, relative to all carbohydrates present in the solution, at least 90, 91, 92, 92.5, 93, 94, 95, 96, 97, 97.5, 98, 99, 99.1, 99.5, or 99.9 wt. % of the glucose. The only carbohydrate added to the solution may be glucose and any inevitable traces of typical contaminants for commercially available glucose. The basic amino acid may preferably be lysine. The solution may comprise, relative to all amino acids present in the solution, at least 90, 91, 92, 92.5, 93, 94, 95, 96, 97, 97.5, 98, 99, 99.1, 99.5, or 99.9 wt. % lysine. The reacting may comprise heating a mixture consisting essentially of water, glucose and lysine at a temperature in a range of from 90 to 100° C., e.g., at least 92.5, 93.33, 95, 96.67, or 99° C. (or any temperature discussed above). The components and reaction conditions should generally not reduce the inhibition of *Aggregatibacter actinomycetemcomitans* any more than 5, 4, 3, 2, 1, 0.5, or 0.1% of a value of the MRPs described in the example for a 30 minute reaction.

The solution may be entirely water (and any inevitable contaminants) or may comprise at least 90, 91, 92, 92.5, 93, 94, 95, 96, 97, 97.5, 98, 99, 99.1, 99.5, or 99.9 wt. % of water, relative to total solvent weight.

The glucose and the basic amino acid may each be present in a concentration range of from 0.75 to 1.5 M in the solution. For example, useful concentrations of glucose in the solution may be, e.g., at least 0.75, 0.8, 0.85, 0.9, 0.95, 1, 1.05, or 1.1 M and/or up to 1.5, 1.33, 1.25, 1.2, 1.15, 1.1, 1.05, 1, or 0.95 M Useful concentrations of basic amino acid (e.g., lysine) in the solution may be, e.g., at least 0.9, 0.95, 1, 1.05, 1.1, 1.15, 1.2, 1.25, 1.3, 1.33, 1.35, or 1.4 M and/or up to 1.75, 1.7, 1.65, 1.6, 1.55, 1.5, 1.45, 1.4, 1.375, 1.35, 1.33, 1.325, 1.3, 1.275, 1.25, or 1.2 M.

The reacting may be conducted for a reaction time in the range of from 20 to 90 minutes, e.g., at least 20, 25, 30, 35, 40, 45, 50, 55, or 60 minutes and/or up to 90, 85, 80, 75, 70, 65, 60, 55, 50, 45, 40, 35, or 30 minutes.

The inhibiting of the growth of *Aggregatibacter actinomycetemcomitans* may comprise allowing no more than 5, 4, 3, 2.5, 2, 1, 0.5, 0.1, 0.01, 0.001, 0.0001, or 0.00001% of the *Aggregatibacter actinomycetemcomitans* growth relative to an untreated AAGC culture space. The inhibiting may be in the heart valves (endocarditis) or in an oral cavity, typically of a human, though optionally in cattle, sheep, goats, horses, camels, or swine.

Aspects of the invention provide isolated Maillard reaction products which may be obtained by a process comprising reacting glucose with a lysine in a molar ratio in a range of from 0.5 to 0.95:1 in water. Useful molar ratios of glucose to amino acid (e.g., lysine) may be 0.5, 0.55, 0.575, 0.6, 0.6125, 0.625, 0.6375, 0.65, 0.6625, 0.675, 0.6875, 0.7, 0.7125, 0.725, 0.7375, 0.75, 0.7625, 0.775, 0.7875, 0.8 (glucose) to 1 (basic amino acid, such as lysine) and/or up to 0.95, 0.9375, 0.925, 0.9125, 0.9, 0.8875, 0.875, 0.8625, 0.85, 0.8375, 0.825, 0.8125, 0.8, 0.7875, 0.775, 0.767, 0.7625, 0.75, 0.7375, 0.733, 0.725, 0.7125, or 0.7 (glucose) to 1 (basic amino acid, such as lysine).

Aspects of the invention provide methods for inhibiting growth of *Aggregatibacter actinomycetemcomitans* comprising contacting the *Aggregatibacter actinomycetemcomitans* with any permutation of the Maillard reaction product or of the inventive Maillard processes described herein.

When heating glucose and lysine in a reaction container such as a reflux pump, every minute there will be an end product that may or may not have an inhibitory activity as shown. Glucose and lysine reactions will not always yield an end product of MRPs that will inhibit wild type *A. actinomycetemcomitans.* Aspects of the invention provide a selection of reactant molar ratios, reaction times, reaction temperatures, reactant concentration, reaction container and/or choice of reactants, to provide a desirable inhibition of wild type *A. actinomycetemcomitans*.

Aspects of the invention employ a reflux pump to process the interaction with HCl, and boiling chips with a specific volume of distilled water, and/or ratio of reactants to solvent, and collecting the resulting product of a particular weight mixture and/or molar ratio of glucose and lysine sample after a particular reaction time, i.e., 30±0.5, 1, 1.5, 2, 2.5, 3, 3.5, 4, 4.5, 5, 7.5, or 10 minutes of processing (or a range with any endpoint therein) and/or 60±0.5, 1, 1.5, 2, 2.5, 5, 6, 7, 7.5, 10, 12.5, 15, 17.5, 20, 25, 30, 35, 40, or 45 minutes of processing (or a range with any endpoint therein). Useful reaction times may be a range combining any of these endpoints. Aspects of the invention involve maintaining the volume of solvent, such as water, within, e.g., 75, 80, 85, 90, 91, 92, 92.5, 93, 94, 95, 96, 97, 97.5, 98, 99, 99.1, 99.5, 99.9, 99.95, or 99.99%, or more, of the initial volume and/or mass, particularly using a reflux pump.

Aspects of the invention employ a reflux/distillation apparatus. The reflux apparatus, generally including a reflux pump, may be a laboratory set-up used to heat a liquid without losing its content volume by evaporation. A spiral tube (coil condenser) may be inside of the top condensation column above the flask that contains the reacting or distilling liquid. During the evaporation of the liquid, the spiral tube cools the evaporate, allowing it to return as liquid to the original flask, as this coil condenser typically has a source of continuous water coming from a sink attached to it with a tube to take in and out the water that cools down the liquid. Thus, whenever the reacting or heating liquid evaporates, it returns to the reaction flask by cooling. During the heating process, there should be boiling chips to prevent the bubbles from occurring as they may cause the loss of the liquid's volume. In addition, the flask that is used to heat the mixture may include one or more openings, e.g., on the side, to collect samples and may be closed with a stopper or the like, to be removed when desired.

Aspects of the invention include reducing or eliminating the formation of bubbles during the heating process using a reflux pump, which may ensure that the Maillard reaction products (MRPs) are prepared at a consistent concentration. Aspects of the invention comprise reaction concentrations and conditions to provide selected MRP end products with inhibitory activity against *A. actinomycetemcomitans*, from the changing classes of products produced continuously, e.g., every 0.1, 0.15, 0.2, 0.25, 0.33, 0.5, 0.67, 0.75, 0.8, 0.9, 1, 1.5, 2, 2.5, 3, 3.5, 5, 7.5, 10, 15, 20, 30, or more minutes, of the process.

Inventive compositions may exclude or may comprise no more than 15, 10, 7.5, 5, 4, 3, 2.5, 2, 1, 0.5, 0.1, 0.01, 0.001, 0.0001, or 0.00001 wt. %, relative to the total composition weight, of one or more antimicrobial agents (beyond the MRPs), antiplaque agents, a whitening agents, cleaning agents, flavoring agents, sweetening agents, adhesion agents, surfactants, foam modulators, abrasives, pH modifying agents, humectants, mouth feel agents, colorants, abrasives, tartar control (anticalculus) agents, fluoride ion sources, saliva stimulating agents, anti-sensitivity agents, antioxidant agents, nutrients, and/or enzymes, individually or in combination. Inventive reaction mixtures and/or compositions may exclude or include no more than 10, 7.5, 5, 4, 3, 2.5, 2, 1, 0.5, 0.1, 0.01, or 0.001 mol. %, relative to the amino acid and/or carbohydrate, or sodium pyrosulfite ($Na_2S_2O_5$).

Inventive compositions may exclude (in free or reacted form) or comprise no more than 15, 10, 7.5, 5, 4, 3, 2.5, 2, 1, 0.5, 0.1, 0.01, 0.001, 0.0001, or 0.00001 wt. %, relative to the total composition weight, of glycine, alanine, valine, leucine, isoleucine, threonine, serine, cysteine, methionine, aspartic acid, asparagine, glutamic acid, glutamine, arginine, histidine, phenylalanine, tyrosine, tryptophan, proline, pyrrolysine, and/or selenocysteine, individually or in combination. Inventive reaction mixtures and/or compositions may exclude (in free or reacted form) or contain no more than 5, 4, 3, 2.5, 2, 1, 0.5, 0.1, 0.01, 0.001, 0.0001, or 0.00001 wt. %, relative to total composition weight, of amino acid dimers, oligomers, peptides, or proteins. The amino acids may be present in natural form, in the unnatural enantiomeric form, or racemic firm. Any of the aforementioned amino acids may be excluded from the reaction mixture, or present in no more than, e.g., 10, 5, 2.5, 1, 0.5, 0.1, 0.01, or 0.001 mol. %, relative to the carbohydrate(s).

Inventive compositions may exclude (in free or reacted form) or comprise no more than 15, 10, 7.5, 5, 4, 3, 2.5, 2, 1, 0.5, 0.1, 0.01, 0.001, 0.0001, or 0.00001 wt. %, relative to the total composition weight, of fructose, galactose, sucrose, maltose, lactose, xylose, ribose, deoxyribose, ribitol, allose, altrose, mannose, gulose, idose, talose, lyxose, arabinose, threose, erythrose, and/or glyceraldehyde. Inventive reaction mixtures may comprise any combination of such carbohydrate, or only one, and the carbohydrate may be in D form (natural), L form, or mixed. Any of the aforementioned carbohydrates may be excluded from the reaction mixture, or present in no more than, e.g., 10, 5, 2.5, 1, 0.5, 0.1, 0.01, or 0.001 mol. %, relative to the amino acid(s).

Inventive compositions may exclude (in free or reacted form) or comprise no more than 15, 10, 7.5, 5, 4, 3, 2.5, 2, 1, 0.5, 0.1, 0.01, 0.001, 0.0001, or 0.00001 wt. %, relative to the total composition weight, of disaccharides, oligosaccharides, and/or polysaccharides, individually or in combination. Aspects of the invention may comprise avoiding microwave, infrared, visible, and/or UV irradiation and/or avoiding convective heating, such as using an autoclave or oven, in the synthesis of the Maillard reaction products (MRPs), or using no more than 3, 2.5, 2, 1.75, 1.5, 1.25, 1, 0.75, 0.67, 0.5, 0.33, 0.25, 0.125, 0.1, or 0.05 hours of any such methods, either alone or in combination.

Aspects of the invention include mouthwash and oral hygiene formulations, such as aqueous formulations containing the MRPs produced as described herein and optionally further including, e.g., up to 25, 20, 15, 10, 7.5, 5, 4, 3, 2, 1, 0.5, or 0.1 wt. %, relative to the total solvent weight, of ethyl alcohol, up to 5, 4, 3, 2.5, 2, 1, 0.5, 0.1, 0.01, 0.001, 0.0001, or 0.00001 wt. %, relative to the total formulation weight, of menthol, cetylpyridinium chloride (optionally substituted with an alternate alkyl chains, e.g., C10, C11, C12, C13, C14, and/or C15, and/or an alternate counter ion, such as fluoride, bromide, and/or iodide), 1,6-bis(4-chlorophenylbiguanido)hexane (chlorhexidine), 1,3-bis(2-ethylhexyl)-5-methylhexahydropyrimidin-5-amine (hexetidine), paracetamol/acetaminophen, acetyl salicylic acid/aspirin, ibuprofen, antibiotic(s), anaesthetic(s), methyl salicylate, 2-methoxy-4-(prop-2-en-1-yl)phenol (eugenol), (E)-3-(4-hydroxy-3-methoxy-phenyl)prop-2-enoic acid (ferulic acid), 3-(3,4-dihydroxyphenyl)-2-propenoic acid (caffeic acid), (E)-3-(3-hydroxy-4-methoxyphenyl)prop-2-enoic acid (isoferulic acid), 4-methoxy-2-[(E)-prop-1-enyl]phenol (pseudoisoeugenol), 2-methoxy-4-(prop-1-en-1-yl)phenol (isoeugenol), phenol, (thymol), (eucalyptol), zinc salt(s), triclosan, tranexamic acid, nystatin, and/or sweetener(s).

Relevant antibiotics may include penicillin (G, K, N, O, of V), amoxacillin, methicillin, nafcillin, oxacillin, cloxacillin, dicloxacillin, flucloxacillin, azithromycin, ampicillin, pivampicillin, hetacillin, bacampicillin, metampicillin, talampicillin, epicillin, carbenicillin, ticarcillin, temocillin, mezlocillin, piperacillin, azlocillin, clavulanic acid, sulbactam, tazobactam, erythromycin, chlortetracycline, tetracycline, cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, latamoxef, cefclidine, cefepime, cefiderocol, cefluprenam, cefoselis, cefozopran, cefpirome, cefquinome, flomoxef, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, nitrocefin, imipenem, meropenem, ertapenem, doripenem, panipenem/betamipron, biapenem, tebipenem, vancomycin, ciprofloxacin, fleroxacin, lomefloxacin, minocycline, nadifloxacin, norfloxacin, ofloxacin, pefloxacin, balofloxacin, grepafloxacin, pazufloxacin, sparfloxacin, temafloxacin, clinafloxacin, sitafloxacin, prulifloxacin, besifloxacin, delafloxacin, rufloxacin, garenoxacin, gatifloxacin, gemifloxacin, levofloxacin, moxifloxacin, danofloxacin, difloxacin, gemifloxacin, trovafloxacin, enrofloxacin, ibafloxacin, marbofloxacin, orbifloxacin, ozenoxacin, sarafloxacin, linezolid, posizolid, tedizolid, radezolid, cycloserine, contezolid, rivaroxaban, sulfafurazole, sulfacetamide, sulfadiazine, sulfadimidine, sulfafurazole, sulfisomidine, sulfamethoxazole, sulfamoxole, sulfanitran, sulfadimethoxine, sulfamethoxypyridazine, sulfametoxydiazine, sulfadoxine, sulfametopyrazine, and/or terephtyl.

Anesthetics may include, for example, articaine, benzocaine, bupivacaine, butamben, chloroprocaine, cinchocaine, cyclomethycaine, dibucaine, etidocaine, levobupivacaine, lidocaine, mepivacaine, oxybuprocaine, piperocaine, pramoxine, prilocaine, proparacaine, propoxycaine, proxymetacaine, ropivacaine, septocaine, (2E,6Z,8E)-N-isobutyl-2,6,8-decatrienamide (spilanthrol), trimecaine, and/or tetracaine, optionally with epinephrine.

Sweeteners may include, for example, sorbitol, erythritol, sucralose, sodium saccharin, xylitol, aspartame, saccharin, cyclamate, stevia, arabitol, brazzein, curculin, fructooligosaccharide, glycyrrhizin, glycerol, hydrogenated starch hydrolysates, inulin, isomalt, isomaltooligosaccharide, isomaltulose, lactitol, mabinlin, maltitol, maltodextrin, mannitol, miraculin, monatin, monellin, osladin, pentadin, polydextrose, psicose, tagatose, thaumatin, acesulfame potassium, advantame, alitame, neohesperidin dihydrochalcone, and/or neotame.

The basis of the need for the treatment by inventive MRPs, beyond *A. actinomycetemcomitans*, may include bacterial, fungal, and/or yeast-based affliction. Additional bacteria treated by inventive MRPs and/or formulations may include streptococcal pharyngitis, i.e., "strep throat," tonsillitis, pharyngitis, laryngitis, gingivitis, ulcerative stomatitis, oral thrush, oral candidiasis (thrush, oropharyngeal candidiasis), pseudomembranous candidiasis, erythematous candidiasis, hyperplastic candidiasis, denture-related stomatitis, angular cheilitis, median rhomboid glossitis, esophageal candidiasis (candidal esophagitis), gastrointestinal candidiasis, and/or respiratory candidiasis.

The formulation may be in the form of a solution, either for liquid topical, subcutaneous, or spray application, a cream/salve for topical application, and/or an aeorsol or gasified form. The formulation may be in a standard mouthwash bottle, e.g., PET, or in syringe for spray or injection. The formulation may be applied for as long as necessary to combat the presence of *A. actinomycetemcomitans*, e.g., for a number of days (1, 2, 3, 4, 5, 6, 7, 8, 9, 10, or more), a number of weeks (1, 1.5, 2, 2.5, 3, 4, 5, or more), or a number of months (1, 2, 3, 4, or more). The administration of inventive formulations may be, e.g., once or twice daily, every 1, 2, 4, 6, 8, or 12 hours, or the like, depending upon the aggressiveness of the treatment regimen and the acuteness of the inhibitory need. The volume of the administration will depend upon the concentration of the formulation, but will generally be in the range of 1 to 250 mL, e.g., at least 1, 2, 2.5, 3, 4, 5, 6, 7.5, or 10 mL and/or up to 250, 200, 150, 125, 100, 75, 50, or 25 mL, for a roughly 0.5 to 2 M, e.g., at least 0.5, 0.67, 0.75, 0.85, 1, 1.1, 1.175, 1.25, or 1.33 M and/or up to 2, 1.75, 1.67, 1.5, 1.33, 1.25, 1.1, or 1 M, solution of MRPs.

The surface treated by the inventive MRPs may be an inanimate surface, such as a seat, table, tablet, screen, or the like, or a human or animal (e.g., cow, horse, pig, goat, sheep, camel, etc.) tissue, such as a mouth or nostril. In the case of oral treatments, the treatment may be on the teeth, gums (gingivae), inferior labial frenulum, salivary duct orifice(s)—sublingual and/or submandibular, lingual frenulum, fauces, tongue, lower lip, palatine tonsile, pharyngopalatine arch, glossopalatine arch, uvula, soft palate, hard palate, superior labial frenulum, and/or upper lip. Inventive injection formulations may also be injected into the gums or any other portion of the oral cavity. Periodontal conditions such as periodontitis may thus be prevented or treated.

Useful formulations may further include menthol, cetylpyridinium chloride, paracetamol, acetyl salicylic acid, ibuprofen, methyl salicylate, 2-methoxy-4-(prop-2-en-1-yl) phenol, 3-(3,4-dihydroxyphenyl)-2-propenoic acid, phenol, thymol, eucalyptol, a zinc salt, triclosan, erythritol, xylitol, sorbitol aspartame, saccharin, sucralose, and/or acesulfame potassium.

Examples

Maillard Reaction Products as Inhibitors of *Aggregatibacter actinomycetemcomitans*

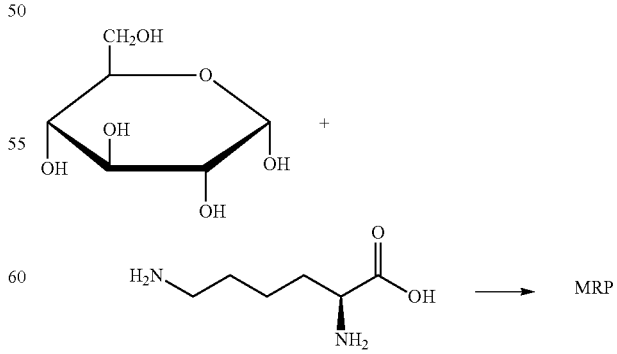

A mixture of 9.01 g (50.0 mmol) of glucose ($C_6H_{12}O_6$, 180.156 g/mol) and 9.50 g (65.0 mmol) of lysine ($C_6H_{14}N_2O_2$, 146.190 g/mol) in 50 mL of water placed in a 250-mL round-bottom flask. The addition is carried out by adding water then glucose, then, lysine, then the pH was adjusted to 7.5 using HCl and NaOH. Then, the boiling chips are added (all in the flask of the reflux pump) The pH was adjusted at 7.5 by using HCl and NaOH to reach a pH of 7.5. At a pH of 7.5, the mixture was heated under reflux in a reflux pump in the presence of boiling chips to make the boiling smoother and prevent bubbles from occurring. A 2 mL sample was collected every 15 minutes for an hour. After an hour of heating, a 2 mL sample was collected every 1 hour. The process was stopped after five hours. Activities were tested for each MRP sample.

Maillard Reaction Products Susceptibility Test

The antibiotic activities of the Maillard reaction product (MRP) samples were determined by the zone of inhibition assay using filter paper disks. From each of the MRP samples, 20 µL was spotted into each disk and allowed to air-dry at room temperature. There were eight MRP samples: 0 minutes, 15 minutes, 30 minutes, 60 minutes, 2 hours, 3 hours, 4 hours, and 5 hours of reaction.

Three *Aggregatibacter actinomycetemcomitans* growth medium (AAGM) plates were prepared and each plate was divided into eight sections. Different amounts of *A. actinomycetemcomitans* cells were spread on each plate: 10 µL, 50 µL, and 100 µL. The MRP-containing disks were loaded onto the plate in each section. The plates were placed in a plastic bag with the following chemicals: 50 mL of 0.5% of HCl (2.5 g HCl, 68.6 mmol) in a beaker and 5 g (59.5 mmol) of baking soda, $NaHCO_3$, on a piece of paper towel was placed outside the beaker. The bag was sealed with heating, e.g., a flame. The paper towel containing the baking soda was placed into the beaker containing HCl in order to release the carbon dioxide, $CO_2$, atmosphere necessary for the *A. actinomycetemcomitans* to grow in the culture. The bag with the plates was incubated at 37° C. for 48 hours.

Only the Maillard reaction product (MRP) samples with the mixture made using a reflux pump, heated at reflux for 30 and 60 minutes exhibited inhibitory activity against *A. actinomycetemcomitans*.

Referring now to the drawings, wherein like reference numerals designate identical or corresponding parts throughout the several views.

FIG. 1 shows a Petri dish divided into 8 sectors containing the *Aggregatibacter actinomycetemcomitans* growth medium (AAGM) plated with the exemplary Maillard reaction product (MRP) samples 20 µL from reaction times of 0 minutes (0), 15 minutes (1), 30 minutes (2), 60 minutes (3), 2 hours (4), 3 hours (5), 4 hours (6), and 5 hours (7), indicating the inhibition (or lack thereof) against *A. actinomycetemcomitans* growth in the culture. As can be seen in the sectors labelled (2) and (3) in FIG. 1, the lack of growth in a ring around the spots for the 30 and 60 minute MRP samples (surrounded in dashed lines) indicates inhibitory activity against *A. actinomycetemcomitans* growth.

Figure 2:
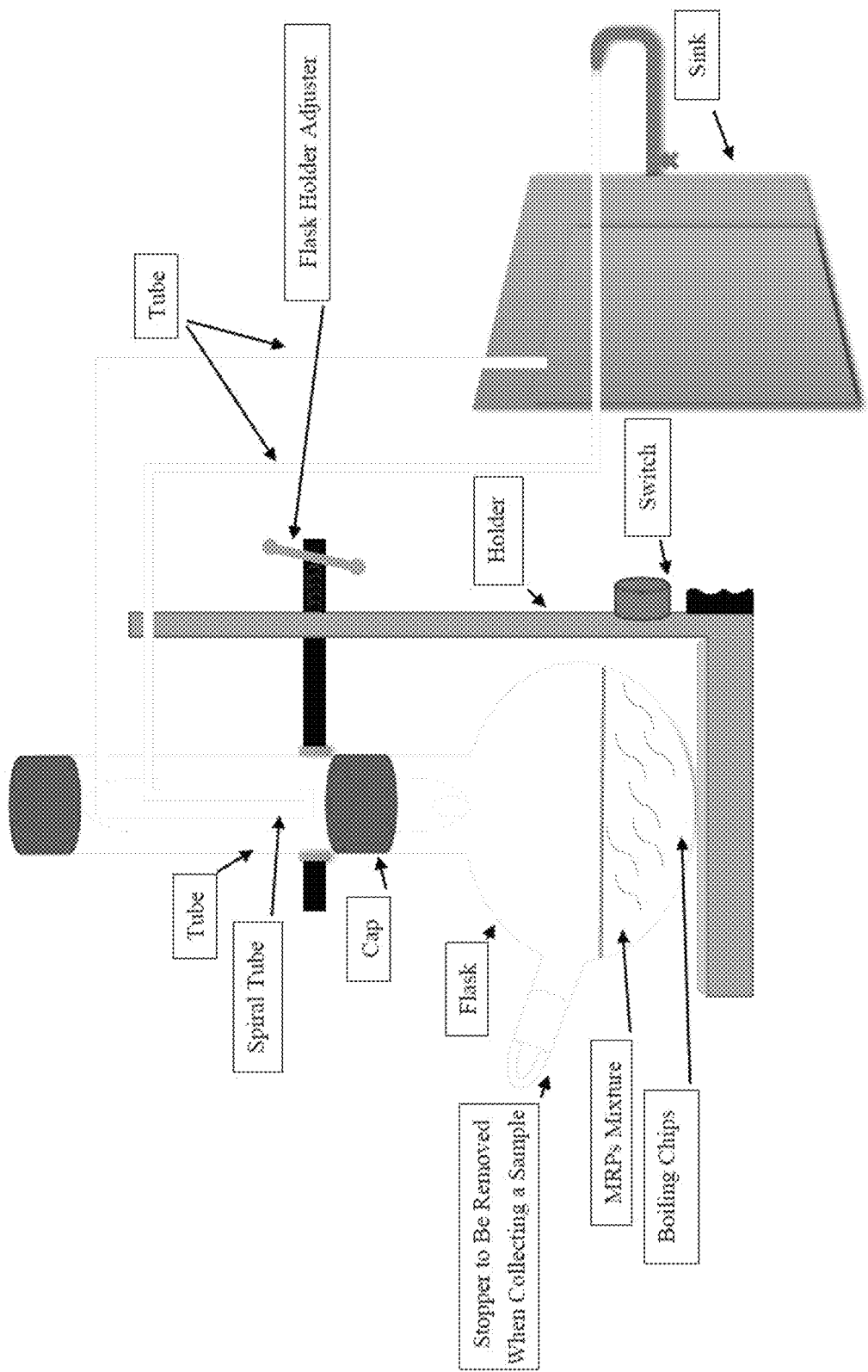
FIG. 2 shows an exemplary reflux reaction set-up which may be used to prepare Maillard reaction products (MRPs) within the scope of the invention.

FIG. 2 shows an exemplary reflux condenser reaction arrangement which may be used according to the invention, indicating a holder, a cooling tube through an inlet and outlet of a distillation column, which may have a coiled glass interior to improve heat exchange (a straight tube is shown for simplicity), a cap, a stopper which may be removed to access the sample containing Maillard reaction products (MRPs) in boiling chips. The cooling may be achieved by any conventional set-up, and a basic sink to outlet laboratory water flow is shown. A vacuum line and pump are not shown, but may be led into a portion of the condensation column/line or as otherwise known in the art.

Such results suggest that a critical range between 15 minutes and 2 hours of reaction time, under conditions similar to those described in the Examples.

Numerous modifications and variations of the present invention are possible in light of the above teachings. It is therefore to be understood that within the scope of the appended claims, the invention may be practiced otherwise than as specifically described herein.

The invention claimed is:

1. A method for treating an infection by *Aggregatibacter actinomycetemcomitans*, which is a gram-negative bacterium, comprising:
   refluxing an aqueous solution comprising glucose and lysine in a molar ratio ranging from 0.5:1 to 0.95:1 at pH ranging from 7.01 to 8.0 and a temperature ranging from 90° C. to 100° C. for a period ranging from 30 to 60 minutes, wherein the glucose and the lysine are each present in a concentration range of from 0.75 to 1.5 M in the solution,
   isolating a Maillard reaction product from said refluxing, and
   contacting a surface of a human oral cavity or a heart infected with *Aggregatibacter actinomycetemcomitans* with the Maillard reaction product.

2. The method of claim 1, wherein the infection is gingivitis.

3. The method of claim 1, wherein the infection is periodontitis.

4. The method of claim 1, wherein the infection is endocarditis.

5. The method of claim 1, wherein the human oral cavity surface is at least one selected from the group consisting of teeth, gums (gingivae), inferior labial frenulum, salivary duct orifice(s), sublingual and/or submandibular surface, lingual frenulum, fauces, tongue, lower lip, palatine tonsile, pharyngopalatine arch, glossopalatine arch, uvula, soft palate, hard palate, superior labial frenulum, and upper lip.

6. The method of claim 1, wherein the subject is human.

7. The method of claim 1, wherein the lysine and glucose are reacted at a molar ratio ranging from 1:1 to 1:1.5.

8. The method of claim 1, wherein the aqueous solution comprises the glucose at a concentration ranging from 0.75M to 1.5M and the lysine at a concentration ranging from 0.9M to 1.2M and at a molar ratio of glucose to lysine of 1:1 to 1:1.5.

9. The method of claim 1, wherein the aqueous solution has a pH ranging from 7.4 to 7.6, and comprises the glucose at a concentration of about 50 mmol/50 ml (1 mmol/ml; 1M) and the lysine at a concentration of about a 65 mmol/50 ml (1.3 mmol/ml; 1.3M).

10. A composition comprising a Maillard reaction product made by refluxing an aqueous solution comprising glucose and lysine in a molar ratio ranging from 0.5:1 to 0.95:1 at pH ranging from 7.01 to 8.0 and a temperature ranging from 90° C. to 100° C. for a period ranging from 30 to 60 minutes, wherein the glucose and the lysine are each present in a concentration range of from 0.75 to 1.5 M in the solution.

11. The composition of claim 10, wherein the aqueous solution comprises lysine and glucose at a molar ratio ranging from 1:1 to 1:1.5.

12. The composition of claim 10, wherein the aqueous solution comprises the glucose at a concentration ranging from 0.75M to 1.5M and lysine at a concentration ranging from 0.9M to 1.2M and wherein a molar ratio of glucose to lysine ranges from 1:1 to 1:1.5.

13. The composition of claim 10, wherein said aqueous solution comprises glucose at a concentration of about 50 mmol/50 ml (1 mmol/ml; 1M) and the lysine at a concentration of about a 65 mmol/50 ml (1.3 mmol/m; 1.3M) and said solution has a pH ranging from 7.4 to 7.6.

14. A method for making a Maillard reaction exhibiting antibacterial activity on by *Aggregatibacter actinomycetemcomitans* comprising:

refluxing an aqueous solution comprising glucose and lysine in a molar ratio ranging from 0.5:1 to 0.95:1 at pH ranging from 7.01 to 8.0 and a temperature ranging from 90° C. to 100° C. for a period ranging from 30 to 60 minutes with boiling chips to prevent bubbles formation, wherein the glucose and the lysine are each present in a concentration range of from 0.75 to 1.5 M in the solution.

15. The method of claim 14, wherein the lysine and glucose are reacted at a molar ratio ranging from 1:1 to 1:1.5.

16. The method of claim 14, wherein the aqueous solution comprises the glucose at a concentration ranging from 0.75M to 1.5M and the lysine at a concentration ranging from 0.9M to 1.2M and at a molar ratio of glucose to lysine of 1:1 to 1:1.5.

17. The method of claim 14, wherein the aqueous solution has a pH ranging from 7.4 to 7.6, comprises the glucose at a concentration of about 50 mmol/50 ml (1 mmol/ml; 1M) and the lysine at a concentration of about a 65 mmol/50 ml (1.3 mmol/ml; 1.3M).

* * * * *